(12) United States Patent
Trieu

(10) Patent No.: US 8,801,790 B2
(45) Date of Patent: Aug. 12, 2014

(54) INTERVERTEBRAL DISC AUGMENTATION AND REHYDRATION WITH SUPERABSORBENT POLYMERS

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2057 days.

(21) Appl. No.: 11/316,974

(22) Filed: Dec. 27, 2005

(65) Prior Publication Data

US 2007/0150061 A1    Jun. 28, 2007

(51) Int. Cl.
*A61F 2/44* (2006.01)

(52) U.S. Cl.
USPC .................................................. 623/17.12

(58) Field of Classification Search
USPC ............ 623/17.11–17.16, 23.58; 604/368
See application file for complete search history.

(56) References Cited

U.S. PATENT DOCUMENTS

| | | | |
|---|---|---|---|
| 4,673,402 A | 6/1987 | Weisman et al. | |
| 4,834,735 A | 5/1989 | Alemany et al. | |
| 4,904,260 A * | 2/1990 | Ray et al. | 623/17.12 |
| 5,147,343 A | 9/1992 | Kellenberger | |
| 5,281,207 A | 1/1994 | Chmielewski et al. | |
| 5,571,189 A * | 11/1996 | Kuslich | 623/17.12 |
| 5,597,873 A | 1/1997 | Chambers et al. | |
| 5,674,295 A | 10/1997 | Ray et al. | |
| 5,824,093 A | 10/1998 | Ray et al. | |
| 5,874,500 A * | 2/1999 | Rhee et al. | 525/54.1 |
| 5,980,504 A | 11/1999 | Sharkey et al. | |
| 6,007,570 A | 12/1999 | Sharkey et al. | |
| 6,073,051 A * | 6/2000 | Sharkey et al. | 607/99 |
| 6,095,149 A | 8/2000 | Sharkey et al. | |
| 6,099,514 A | 8/2000 | Sharkey et al. | |
| 6,126,682 A | 10/2000 | Sharkey et al. | |
| 6,132,465 A | 10/2000 | Ray et al. | |
| 6,187,048 B1 * | 2/2001 | Milner et al. | 623/17.12 |
| 6,231,605 B1 * | 5/2001 | Ku | 623/11.11 |
| 6,245,107 B1 * | 6/2001 | Ferree | 606/279 |
| 6,280,475 B1 * | 8/2001 | Bao et al. | 623/17.16 |
| 6,306,177 B1 * | 10/2001 | Felt et al. | 623/23.6 |
| 6,306,418 B1 * | 10/2001 | Bley | 424/422 |
| 6,352,557 B1 * | 3/2002 | Ferree | 623/17.11 |
| 6,402,784 B1 * | 6/2002 | Wardlaw | 623/17.11 |
| 6,423,332 B1 * | 7/2002 | Huxel et al. | 424/422 |
| 6,443,988 B2 * | 9/2002 | Felt et al. | 623/17.12 |
| 6,602,291 B1 | 8/2003 | Ray et al. | |
| 6,692,528 B2 | 2/2004 | Ward et al. | |
| 6,719,797 B1 * | 4/2004 | Ferree | 623/17.16 |
| 6,818,018 B1 * | 11/2004 | Sawhney | 623/11.11 |
| 6,881,228 B2 | 4/2005 | Zdeblick et al. | |
| 7,611,542 B2 * | 11/2009 | Bourne et al. | 623/23.72 |
| 2002/0029083 A1 | 3/2002 | Zucherman et al. | |
| 2002/0045942 A1 * | 4/2002 | Ham | 623/17.12 |
| 2002/0082699 A1 | 6/2002 | Ward et al. | |
| 2002/0183848 A1 | 12/2002 | Ray et al. | |
| 2003/0040800 A1 | 2/2003 | Li et al. | |
| 2004/0054414 A1 | 3/2004 | Trieu et al. | |

(Continued)

*Primary Examiner* — Mary Hoffman
(74) *Attorney, Agent, or Firm* — Sorell Lenna & Schmidt LLP

(57) ABSTRACT

The embodiments provide a method for treating an intervertebral disc having a nucleus pulposus and an annulus fibrosis, using one or more superabsorbent polymers. Additionally, the embodiments provide a method for bulking up an intervertebral disc having a nucleus pulposus and an annulus fibrosis, using one or more superabsorbent polymers. The methods comprise introducing an amount of the superabsorbent polymers into the intervertebral disc space without removing nucleus pulposus or annulus fibrosis material.

40 Claims, 3 Drawing Sheets

(56) References Cited

U.S. PATENT DOCUMENTS

| | | |
|---|---|---|
| 2004/0068268 A1* | 4/2004 | Boyd et al. .................. 606/92 |
| 2004/0102774 A1 | 5/2004 | Trieu |
| 2004/0133280 A1 | 7/2004 | Trieu |
| 2004/0140264 A1 | 7/2004 | Ward et al. |
| 2004/0186471 A1 | 9/2004 | Trieu |
| 2004/0210315 A1 | 10/2004 | Li et al. |
| 2004/0220672 A1* | 11/2004 | Shadduck ............... 623/17.16 |
| 2004/0228901 A1 | 11/2004 | Trieu et al. |
| 2005/0031666 A1 | 2/2005 | Trieu |
| 2005/0070913 A1* | 3/2005 | Milbocker et al. ............. 606/92 |
| 2005/0085916 A1 | 4/2005 | Li et al. |
| 2005/0119754 A1 | 6/2005 | Trieu et al. |
| 2005/0203474 A1 | 9/2005 | Flohr |
| 2006/0089721 A1* | 4/2006 | Muhanna et al. ......... 623/17.16 |
| 2006/0206209 A1* | 9/2006 | Cragg et al. ............. 623/17.16 |
| 2007/0093905 A1* | 4/2007 | O'Neil et al. ............ 623/17.16 |
| 2007/0179620 A1* | 8/2007 | Seaton et al. ............ 623/17.16 |

\* cited by examiner

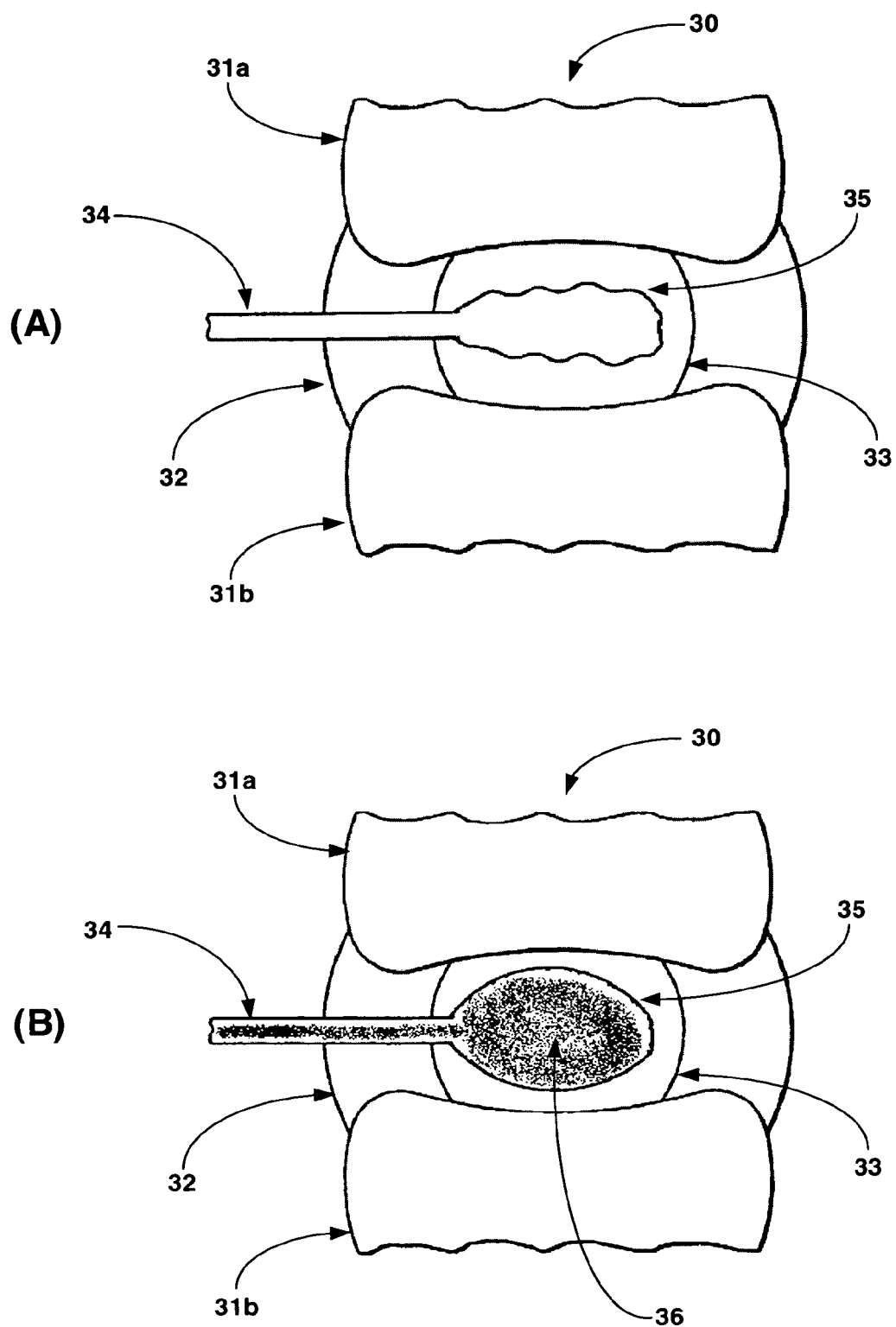

INTERVERTEBRAL DISC AUGMENTATION AND REHYDRATION WITH SUPERABSORBENT POLYMERS

FIELD OF THE INVENTION

Embodiments relate to apparatus, methods, and devices for augmentation of the intervertebral disc space. More specifically, embodiments relate to methods of using superabsorbent polymers to treat an intervertebral disc space.

BACKGROUND

The intervertebral disc functions to stabilize the spine and to distribute forces between vertebral bodies. The intervertebral disc is composed primarily of three structures: the nucleus pulposus, the annulus fibrosis, and two vertebral end-plates. These components work together to absorb the shock, stress, and motion imparted to the spinal column. The nucleus pulposus is an amorphous hydrogel in the center of the intervertebral disc. The annulus fibrosis, which is composed of highly structured collagen fibers, surrounds and constrains the nucleus pulposus within the center of the intervertebral disc. The vertebral end-plates, composed of hyalin cartilage, separate the disc from adjacent vertebral bodies and act as a transition zone between the hard vertebral bodies and the soft disc.

The nucleus pulposus typically contains a negatively charged proteoglycan component. Proteoglycans are glycoproteins with many polysaccharide side chains, and have properties that are more like typical polysaccharides than proteins. The proteoglycan component of the nucleus pulposus associates with water to form a hydrated gel. Water may reach the nucleus pulposus from sieve-like pores in the end plates. The resulting osmotic pressure within the intervertebral disc causes it to expand axially (i.e., vertically), driving the adjacent vertebrae apart. On the other hand, mechanical movements resulting in axial compression, flexion, and rotation of the vertebrae exert forces on the intervertebral disc, which tends to drive water out of the nucleus pulposus. Water movement into and out of an intervertebral disc under the combined influence of osmotic gradients and mechanical forces is important for maintaining disc health. In a normal healthy nucleus pulposus, water comprises between about 80% to about 90% of the nucleus's total weight.

Intervertebral discs may be displaced or damaged due to trauma, disease, and the normal aging process. Intervertebral discs undergoing degeneration typically experience dehydration relatively early in the degeneration process. During dehydration of the intervertebral disc, the water associated with the proteoglycan hydrogel comprising the nucleus pulposus of the disc may be lost. Dehydration of the nucleus may result in collapse of the disc space and reduced disc space height. Reduced disc space height may lead to instability of the spine, decreased mobility, and back and leg pain.

Several general strategies have been proposed in order to restore disc height in a dehydrated intervertebral disc. In one strategy, the disc is treated by inducing repair or regeneration of the nucleus with a biological treatment. Biological treatments include a broad variety of treatment regimens such as the implantation of nucleus pulposus cells harvested from healthy intervertebral discs, steroidal injections to induce cell proliferation, genetic treatments to induce and/or increase proteoglycan production by the pulposus cells, and so forth. Unfortunately, effective biological treatments appear to be many years away from commercial development and routine use.

In another strategy to treat dehydrated intervertebral discs, a portion or all of the nucleus is removed and a prosthetic nucleus device is implanted in the intervertebral disc space to augment or completely replace the dehydrated nucleus. Alternatively, a total disc replacement ("TDR") operation may be performed wherein not just the dehydrated nucleus but the entire intervertebral disc is removed and replaced with a prosthesis. However, nucleus and TDR replacements remain unproven. Also, even when minimally invasive surgical techniques are used, these surgeries are relatively difficult to perform and inflict a good deal of trauma on the patient, resulting in increased post-surgical recovery times and disability. Additionally, the complexity of currently available intervertebral prostheses necessitates careful and meticulous consideration of the patient's unique prognosis to determine which prosthesis is most likely to result in a positive therapeutic outcome.

The description herein of problems and disadvantages of known apparatuses, methods, and devices is not intended to limit the embodiments to the exclusion of these known entities. Indeed, embodiments may include one or more of the known apparatus, methods, and devices without suffering from the disadvantages and problems noted herein.

BRIEF SUMMARY

What is needed is an improved method to treat an intervertebral disc. In particular, what is needed is a relatively simple, fast, and easy method to treat a dehydrated intervertebral disc. Furthermore, what is needed is a method to treat dehydrated intervertebral discs that is minimally invasive and easily reversible relative to other treatment regimens.

Therefore, in accordance with one embodiment, there is provided a method for treating an intervertebral disc using one or more superabsorbent polymers. The intervertebral disc has a nucleus pulposus and an annulus fibrosis. The method comprises introducing the superabsorbent polymers into the intervertebral disc space without removing nucleus pulposus or annulus fibrosis material, thereby rehydrating the intervertebral disc.

In accordance with another embodiment, there is provided a method for bulking up an intervertebral disc using one or more superabsorbent polymers. The intervertebral disc has a nucleus pulposus and an annulus fibrosis. The method comprises introducing the superabsorbent polymers into the intervertebral disc space without removing nucleus pulposus or annulus fibrosis material, thereby maintaining and/or increasing the disc height, the disc volume, or the intra-discal pressure.

These and other features and advantages will be apparent from the description provide herein.

BRIEF DESCRIPTION OF THE DRAWINGS

FIG. 3, embodiments A and B, illustrates an exemplary inflatable member to which a superabsorbent polymer is delivered to treat an intervertebral disc space.

DETAILED DESCRIPTION OF THE PREFERRED EMBODIMENTS

Figure 1:
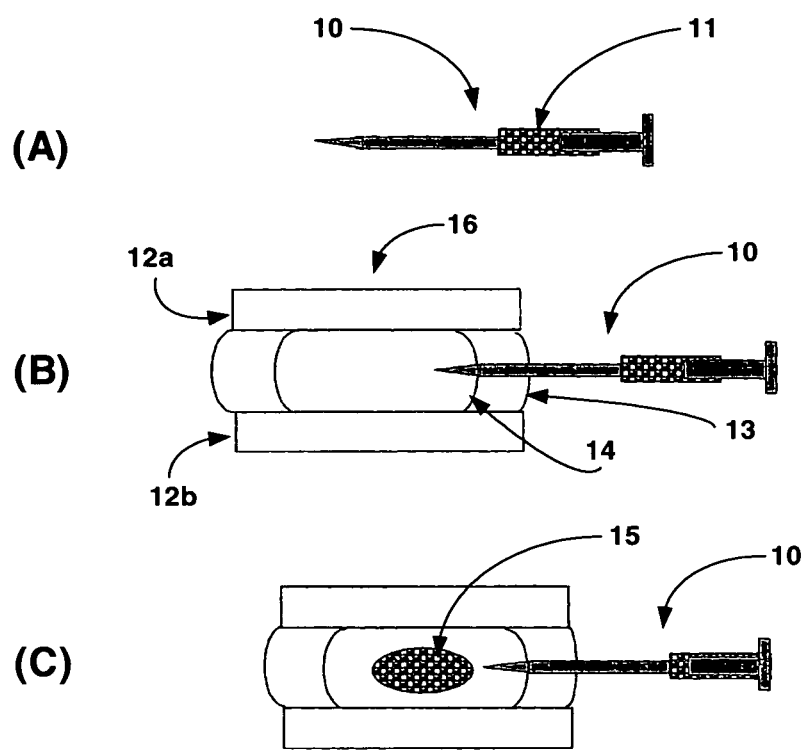
FIG. 1, embodiments A, B, and C, illustrates an exemplary "wet" delivery method for introducing superabsorbent polymers to the intervertebral disc space.

The following description is intended to convey a thorough understanding of the various embodiments by providing a number of specific embodiments and details involving treatment of the intervertebral disc space. It is understood, however, that the embodiments are not limited to these specific preferred descriptions and details, which are exemplary only. It is further understood that one possessing ordinary skill in the art, in light of known systems and methods, would appreciate the use of the embodiments for their intended purpose and benefits in any number of alternative embodiments.

As used herein and in the appended claims, the singular forms "a," "an," and "the" include plural reference unless the context clearly dictates otherwise. Thus, for example, a reference to "a superabsorbent polymer" includes a plurality of such polymers, and a reference to "a polyelectrolyte" is a reference to one or more polyelectrolytes, and so forth.

As used herein, the term "polyelectrolytes" refers to long linear chains of polymers with ionic groups along the molecular chains. The polyelectrolytes may or may not also have side chains on the polymers. Because of the presence of the ionic groups, polyelectrolytes attract water (i.e., are hydrophilic) and then eventually dissolve when placed in sufficiently large quantities of water. Polyelectrolytes are, at most, only slightly crosslinked.

The expression "superabsorbent polymers" ("SAPs") refers to generally water-insoluble but water-swellable polymeric substances capable of imbibing, absorbing, or gelling extremely large amounts of fluids, such as water and aqueous solutions. Typically, superabsorbent polymers are produced by crosslinking hydrophilic polymers. Because of their crosslinked hydrophilic polymer structure, superabsorbent polymers absorb fluids without dissolving into solution. An exemplary type of superabsorbent polymer is crosslinked polyelectrolytes.

In a preferred embodiment, superabsorbent polymers are capable of absorbing fluids in an amount that is at least ten times the weight of the SAPs in their dry form, at atmospheric pressure. In another preferred embodiment, superabsorbent polymers are capable of absorbing fluids in an amount that is at least twenty times the weight of the SAPs in their dry form, at atmospheric pressure. In still another preferred embodiment, superabsorbent polymers are capable of absorbing fluids in an amount that is at least twenty-five times the weight of the SAPs in their dry form, at atmospheric pressure. The fluid is taken into the molecular structure of the superabsorbent polymer and not simply contained in pores from which it can be expressed by squeezing.

The water absorption and water retention characteristics of superabsorbent polymers are due to the presence in the polymer structure of ionizable functional groups. For example, some carboxylated, phosphonoalkylated, sulphoxylated, and phosphorylated polymers are useful as superabsorbent polymers. The ionizable functional groups may be left in their free acid or base forms (i.e., "underneutralized superabsorbent polymers" or "uSAPs"), or else may be neutralized to yield the salt form of the groups.

Preferably, the ionizable functional groups undergo dissociation upon contact with water. In the dissociated state, the superabsorbent polymer chains may have a series of functional groups attached to it which groups have the same electric charge and thus repel one another. This may lead to expansion of the superabsorbent polymer structure which, in turn, permits further absorption of water molecules. This expansion, however, is subject to the constraints provided by the cross-links in the superabsorbent polymer structure, which are sufficient to prevent dissolution of the SAP.

The degree of cross-linking of superabsorbent polymers can be an important factor in establishing their absorbent capacity and gel strength. Absorbent polymers useful in the embodiments described herein preferably have adequately high sorption capacity, and relatively low gel strength compared to the hydrogels used in nucleus and intervertebral disc replacement devices. Gel strength relates to the tendency of the swollen polymer to deform under an applied stress. A low gel strength may be desirable because the retained, or original, nucleus pulposus and annulus fibrosis of the intervertebral disc may be intended to provide the majority of the strength in the intervertebral disc. The superabsorbent polymers, in comparison, may be intended to offer little or no structural strength to the intervertebral disc, other than that provided by the SAPs' ability to rehydrate the disc and the bulking effect of introducing the SAPs to the disc space.

In a preferred embodiment, the superabsorbent polymers are no more than about 30% crosslinked. In another preferred embodiment, the superabsorbent polymers are not more than about 20% crosslinked. In still another preferred embodiment, the superabsorbent polymers are not more than about 10% crosslinked. In these embodiments, the relatively low percentage of crosslinked polymer chains ensures that the superabsorbent polymers are weak and do not provide substantial mechanical strength to the intervertebral disc, other than the strength provided by the SAPs' ability to absorb fluids and rehydrate the disc space. Additionally, the low crosslinking of the superabsorbent polymers helps to ensure that the polymers are able to expand and absorb large amounts of water.

The superabsorbent polymers may be lightly crosslinked by including the appropriate amount of a suitable crosslinking monomer during polymerization of the constituent polymer chains. Alternatively, the polymer chains comprising the superabsorbent polymers may be crosslinked after polymerization of the chains by reaction with a suitable crosslinking agent. Examples of crosslinking agents include, but are not limited to:

(i) polyfunctional ethylenically unsaturated cross-linking agents such as N,N'-methylenebisacrylamide, polyethylene glycol di(meth)acrylate, trimethylolpropane tri(meth)acrylate, and divinyl benzene;

(ii) polyfunctional cross-linking agents such as epichlorohydrin and related halo epoxy compounds, diglycidyl ether compounds, diisocyanates, polyaldehydes, and polyfunctional amines and imines;

(iii) triallylamine, diaziridine compounds, acrylic acid, diiodopropane, dichloropropane, ethylene glycol diglycidyl ether, alkylenebisacylamides, di- and poly-halogenated compounds, and di- or poly-epoxy compounds; and (v) mixtures and combinations thereof.

Superabsorbent polymers may include polymer chains that are synthetic, natural, and hybrid synthetic-natural polymers. Natural polymers include polysaccharides such as cellulose, starch, and regenerated cellulose that are modified to be carboxylated, phosphonoalkylated, sulphoxylated or phosphorylated, thereby causing the polymer chains to become highly hydrophilic. Synthetic polymers include, but are not limited to, polyacrylates. U.S. Pat. No. 5,147,343 issued to Kellenberger, U.S. Pat. No. 4,673,402 issued to Weisman, U.S. Pat. No. 5,281,207 issued to Chmielewski et al., and U.S. Pat. No. 4,834,735 issued to Alemany, et al. disclose many types of SAPs and methods for making them, and are incorporated herein by reference in their entirety in accordance with the described embodiments.

Some exemplary superabsorbent polymers may include, but are not limited to:

(i) polyacrylic acid, polymethacrylic acid, polymaleic acid, copolymers thereof, and alkali metal and ammonium salts thereof;

(ii) graft copolymers of starch and acrylic acid, starch and saponified acrylonitrile, starch and saponified ethyl acrylate, and acrylate-vinyl acetate copolymers saponified;
(iii) polyvinylpyrrolidone, polyvinyl alkylether, polyethylene oxide, polyacrylamide, and copolymers thereof;
(iv) copolymers of maleic anhydride and alkyl vinylethers;
(v) saponified starch graft copolymers of acrylonitrile, acrylate esters, vinyl acetate, and starch graft copolymers of acrylic acid, methyacrylic acid, and maleic acid;
(vi) the product of crosslinking acrylamide with backbones of kappa-carrageenan and soldium alginate using methylenebisacrylamide and potassium persulfate;
(vii) the product of crosslinking, using a bifunctional crosslinking reagent, an acyl-modified protein matrix such as soy protein isolate which has been acyl-modified by treatment with ethylenediaminetetraacetic acid dianhydride; and
(viii) mixtures and combinations thereof.

It is believed that the rehydrated nucleus pulposus functions in a manner that can be analogized to a tire. By increasing the water affinity of the intervertebral disc (i.e., introducing a superabsorbent polymer therein) it is thought that the hydrodynamic pressure inside of the disc space may be increased. The water inside of the disc is like the air inside of a tire, and the annulus functions like the tire itself. Increasing the hydrodynamic pressure inside of the intervertebral disc space inflates the disc. The load placed on the disc is carried by the annulus, which preferably is sufficiently healthy, intact, and competent to retain the water, superabsorbent polymers, and nucleus tissue inside of the disc space. Therefore, it is thought that the superabsorbent polymers, when delivered to the disc space, bear little, if any, of the load of the intervertebral disc. Instead, it is thought that the annulus fibrosis and rehydrated nucleus pulposus bear the majority of the load of the disc, as would occur in a normal, healthy disc. Thus, the superabsorbent polymers may not and preferably do not need a high degree of structural strength.

Because the superabsorbent polymers act to attract and maintain water in the disc space, and thereby rehydrate the nucleus pulposus, it is desirable that healthy annulus fibrosis and endplates be present in the intervertebral disc. Otherwise, delivery of a superabsorbent polymer to the intervertebral disc may not result in the desired level of rehydration and augmentation. In particular, a compromised annulus fibrosis or endplate may not be capable of retaining the water that is attracted to the superabsorbent polymer, the superabsorbent polymer itself, and the nucleus tissue. Therefore, in the case of a significantly compromised annulus fibrosis or endplate, little or no rehydration of the nucleus may occur even after introduction of a superabsorbent polymer to the disc space.

Therefore, the methods provided by the embodiments herein preferably are used to treat patients with mild to moderate disc degeneration and an essentially intact and competent annulus fibrosis. As explained herein, delivery of the superabsorbent polymers may be accomplished with little or no additional injury to the annulus fibrosis. The methods provided herein may be especially useful for patients that are not good candidates for nucleus replacement surgery, spinal fixation, total disc replacement, spinal fusion, and other surgical regimens for the treatment of degenerated intervertebral discs.

Accordingly, embodiments provide a method for treating an intervertebral disc having a nucleus pulposus and an annulus fibrosis, using one or more superabsorbent polymers. The method comprises introducing the superabsorbent polymers into the intervertebral disc space without removing nucleus pulposus or annulus fibrosis material, thereby rehydrating the intervertebral disc. The intervertebral disc may be a cervical, lumbar, or thoracic disc.

Furthermore, embodiments provide a method for bulking up an intervertebral disc having a nucleus pulposus and an annulus fibrosis, using one or more superabsorbent polymers. The method comprises introducing the superabsorbent polymers into the intervertebral disc space without removing nucleus pulposus or annulus fibrosis material, thereby increasing the height, the volume, and/or the intra-discal pressure of the disc. The intervertebral disc may be a cervical, lumbar, or thoracic disc.

Preferably, the methods provided herein are used to rehydrate the intervertebral disc until equilibrium swelling is attained. Additionally, the methods may be useful to treat an intervertebral disc that already has at least partially collapsed. Preferably, the amount of superabsorbent polymer placed in the intervertebral disc is sufficient to increase the disc height, and more preferably to restore the disc's natural height. Skilled artisan will be capable of determining the desired amount of superabsorbent polymer based on a number of factors, including, for example, the degree of disc degeneration, the age, weight, and health of the patient, and the degree of restoration required. Additionally, the methods provided herein may be used to slow the rate of progressive collapse of an intervertebral disc and/or maintain the height of an intervertebral disc experiencing progressive collapse.

The superabsorbent polymers may be delivered to the disc space in a variety of forms, such as beads, fibers, flakes, granules, microspheres, nano-particles, particles, pellets, platelets, powder, randomly shaped particles, rods, chunks, pieces, and so forth. Preferably, whatever form the superabsorbent polymers are in, the largest dimension of the superabsorbent polymer is not more than about 5 mm, more preferably no more than about 2 mm, and most preferably no more than about 1 mm. The superabsorbent polymers may be delivered to the intervertebral disc space, for example, utilizing "dry" and "wet" delivery methods.

In the "wet" delivery method, the superabsorbent polymers may be fluidized, for example, by mixing the superabsorbent polymers with a medium to form a gel, suspension, paste, solution, mixture, etc. of the superabsorbent polymers that is sufficiently fluid in nature to be delivered through a needle, catheter, trocar, cannula, syringe, caulk gun-like device, barrel-plunger device, other injection or extrusion devices, or any other such applicable delivery device. For example, the delivery device may be used to pierce or puncture the annulus fibrosis in order to reach the interior of the disc space and nucleus pulposus. If desired, a more rigid, larger diameter cannula may be used to gain access to the outer disc annulus, and a smaller diameter needle may be used to puncture the annulus and inject the superabsorbent polymer into the disc space. Additionally, if desired, a more rigid instrument such as a stylet may be used to guide the delivery device through the body and towards the disc space.

The flowable superabsorbent polymers (e.g., a superabsorbent polymer-containing gel or suspension) may be introduced into the delivery device and subjected to pressure or mechanical forces in order to force the superabsorbent polymers to exit the distal end of the delivery device and enter the intervertebral disc space. In an exemplary embodiment, a syringe filled with the superabsorbent polymer in the form of a gel, suspension, paste, solution, mixture, etc. may be used to force the superabsorbent polymer through the delivery device (e.g., a needle, cannula, catheter, trocar, etc.) and into the disc space.

It may be desirable to place the patient under traction in order to reduce intra-discal pressure before, during, and after injection. It also may be desirable to distract the upper and lower vertebral bodies using a minimally-invasive disc distraction device or external traction devices. This may be advantageous in order to reduce the injection pressure necessary to affect delivery of the superabsorbent polymer, increase the injectable volume of the disc space, reduce the potential for post-delivery leakage of the superabsorbent polymer, and so forth. When sufficient superabsorbent polymer has been introduced into the disc space, the delivery device may be removed.

Fluids for delivery of the superabsorbent polymers to the disc space include, but are not limited to: water, saline, vegetable oils (e.g., canola, corn, and peanut oil), olive oil, alcohols, triacetin, diacetin, tributyrin, triethyl citrate, tributyl citrate, acetyl triethyl citrate, acetyl tributyl citrate, triethylglycerides, glycerin, triethyl phosphate, diethyl phthalate, diethyl tartrate, mineral oil, polybutene, silicone fluid/oil, glylcerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide (DMSO), tetrahydrofuran, caprolactam, decylmethylsulfoxide, oleic acid, 1-dodecylazacycloheptan-2-one, and mixtures and combinations thereof.

Preferably, the delivery device is of a small cross-section so that no larger a defect than is necessary is created in the annulus fibrosis or endplate when it is pierced. This is desirable because it is thought that the annulus fibrosis is slow to heal, and a puncture in the annulus may allow fluids to escape from the intervertebral disc space. Therefore, it is may be desirable that the flowable superabsorbent polymer not experience significant swelling prior to delivery to the disc space. For example, if the superabsorbent polymer is in a granular form, significant swelling of the superabsorbent polymer grains when they are mixed with a medium to fluidize them may prevent the flowable superabsorbent polymer from being capable of passing through a small-diameter needle or catheter. This, in turn, would necessitate the use of a larger-diameter needle or catheter to deliver the flowable superabsorbent polymer, and result in greater damage to the annulus fibrosis.

Thus, it may be desirable to fluidize the superabsorbent polymer with non-aqueous fluids or a mixture of non-aqueous and aqueous fluids. Doing so may reduce the superabsorbent polymer's viscosity so that it is sufficiently flowable to facilitate introduction to the disc space, but without causing pre-delivery swelling of the superabsorbent polymer.

The delivery of a flowable superabsorbent polymer is exemplarily illustrated in FIG. 1, embodiments A, B, and C. In embodiment A, a syringe/needle assembly 10 is provided as a delivery device with a superabsorbent polymer 11 that has been mixed with a fluid, either aqueous and/or non-aqueous. In embodiment B, the syringe/needle assembly 10 penetrates the annulus fibrosis 13 of the intervertebral disc space 16 having end plates 12a and 12b. In the preferred embodiment depicted in FIG. 1, embodiment B, the distal end of the syringe/needle assembly 10 is inserted into the nucleus pulposus 14 of the disc for direct delivery of the superabsorbent material. The syringe is depressed to expel the superabsorbent material 15, as shown in embodiment C, and then removed from the disc space. Optionally, the annulus fibrosis may be treated to heal any injury incurred due to the insertion of the syringe, as explained herein.

In one embodiment, the superabsorbent polymers that are used to augment and rehydrate the intervertebral disc comprise polyelectrolytes. Because of the presence of ionizable groups in polyelectrolytes, it is thought that the capacity of polyelectrolytes to absorb and/or attract water and other aqueous mediums may be sensitive to factors such as the pH of the aqueous medium, ionic strength of the aqueous medium, electric fields, and temperature. Desirably, these variables may be adjusted in order to affect the behavior of the polyelectrolytes, especially the behavior of crosslinked polyelectrolytes that comprise a flowable superabsorbent polymer that is to be delivered to the intervertebral disc space. Preferably, these variables may be adjusted in order to reduce the volume of the superabsorbent polymer-containing gel or solution in order to facilitate delivery of the superabsorbent polymers through small-diameter needles and catheters.

For example, a lower pH aqueous medium may be mixed with the polyelectrolyte-comprising superabsorbent polymers prior to delivery to the disc space. Because the lower pH aqueous medium may reduce ionization of the polyelectrolytes, it may reduce the polyelectrolytes' affinity for water. Thus, the superabsorbent polymer may have less of a tendency to swell when combined with a low-pH medium to fluidize the superabsorbent polymer prior to delivery to the disc space. A decreased tendency to swell may be desirable in order to deliver the superabsorbent polymer through a small-diameter needle or catheter.

The ionic strength of the medium that is used to fluidize the polyelectrolyte-comprising superabsorbent polymer for delivery to the disc space also may be adjusted in order to discourage swelling of the polyelectrolytes prior to introduction into the disc space. For example, a hypertonic saline medium or a medium with a high concentration of ionic salts may be used to fluidize the superabsorbent polymer without inducing significant swelling of the polyelectrolytes. After insertion, the saline or salt medium may diffuse out of the disc and be replaced with body fluids, which may dilute the saline or salt medium and reduce its ionic strength. The superabsorbent polymer then can absorb the lowered-ionic strength medium, leading to rehydration of the nucleus.

In another embodiment, an electric field may be used to reduce the polyelectrolytes' ability to ionize in solution, and thus reduce their affinity for water, during delivery to the disc space. Again, this may be useful in order to reduce the swelling of the polyelectrolyte-comprising superabsorbent polymer during delivery to the disc space, thereby facilitating delivery of the superabsorbent polymer through a small-diameter needle or catheter. After delivery to the disc space, the electric field may be removed to restore the superabsorbent polymer's ability to ionize, and thus its affinity for water.

Finally, the temperature of the polyelectrolyte-comprising superabsorbent polymer and the temperature of the medium used to fluidize it may be adjusted in order to decrease the polyelectrolytes' affinity for water during delivery to the disc space. Adjustment of these four variables (pH, ionic strength, electric fields, and temperature) to reduce the polyelectrolyte-comprising superabsorbent polymer's hydrophilicity during delivery to the disc space may be especially desirable when the superabsorbent polymer is in a comparatively bulky, solid form (e.g., microspheres).

Another way in which the superabsorbent polymers may be delivered to the disc space is via a "dry" delivery method, without rendering the superabsorbent polymer flowable. According to the dry delivery method, the superabsorbent materials may be packed into a small diameter delivery device such as a needle, catheter, trocar, cannula, etc. in the form of a dry powder, particulates, small chunks, pellets, short rods, chunks, pieces, and so forth. No fluid is mixed with the superabsorbent materials prior to delivery to the intervertebral disc space. Preferably, the delivery device has a diameter of no more than about 3 mm, more preferably no more than about 2 mm, and most preferably no more than about 1 mm.

The annulus fibrosis may be punctured and the delivery device inserted. Preferably, the delivery device itself may be used to puncture the annulus fibrosis, especially when the delivery device is a needle or trocar. The distal end of the delivery device then may be brought close to the center of the disc space. A plunger, stylet, or other such device may be used to extrude or push the dry superabsorbent polymer material through the delivery device and into the disc space. When sufficient superabsorbent polymer material has been delivered to the disc space, the delivery device may be removed.

It is believed that, upon delivery to the intervertebral disc space, the superabsorbent polymers will attract water to the disc space until equilibrium swelling is achieved. Preferably, sufficient superabsorbent polymer is delivered to the disc space to cause the disc to increase in height, and more preferably to return to its natural height. In one embodiment, the superabsorbent polymers may be used to treat a degenerated intervertebral disc that has at least partially collapsed. Introduction of the SAPs to the disc space may cause the height of the at least partially collapsed disc space to increase. In another embodiment, the superabsorbent polymers may be used to treat a degenerated intervertebral disc that is experiencing progressive disc collapse. Introduction of the SAPs to the disc that is experiencing progressive collapse may reduce the rate of collapse. Also, introduction of the SAPs to the disc that is experiencing progressive collapse may maintain the height of the disc.

In one embodiment, "wet" delivery of the superabsorbent polymer is accomplished by mixing the polymer material with an aqueous medium such as water, saline solution, a contrast media containing water, and so forth. The presence of water in the aqueous medium may cause pre-delivery swelling of the superabsorbent polymer. After delivery to the intervertebral disc space, it is thought that the superabsorbent polymer will either exude water into the disc space and nucleus, or else will continue to attract water to the disc space. In either case, it is believed that the end result of introducing the superabsorbent polymer to the intervertebral disc space will be to increase the hydrodynamic pressure in the disc space, rehydrate the nucleus, and restore the disc, such as restoring the disc space's natural height, volume, and load support.

In another embodiment, "wet" delivery of the superabsorbent polymer is accomplished by mixing the superabsorbent polymer material with a non-aqueous medium. It is believed that, because of the superabsorbent polymers' limited absorption of the non-aqueous medium and limited swelling, a slurry or suspension may be formed given a sufficient amount of the non-aqueous solution. It also is believed that, after delivery to the intervertebral disc space, the non-aqueous solution will diffuse out of the disc space and be replaced by water attracted by the highly hydrophilic superabsorbent polymer. The net result may be increased water in the disc space and the attendant beneficial effects thereof that have been described herein.

In still another embodiment, "wet" delivery of the superabsorbent polymer is accomplished by mixing the polymer material with a mixture of non-aqueous and aqueous mediums. A mixture of non-aqueous and aqueous mediums may be useful where is it desired to deliver the superabsorbent polymers with minimal pre-delivery swelling, but the superabsorbent polymers are not sufficiently soluble in purely non-aqueous mediums to be brought into solution and/or fluidized. Therefore, by mixing a sufficient amount of an aqueous medium with the non-aqueous medium, the superabsorbent polymers may be brought into solution and fluidized but with a minimal amount of pre-delivery swelling. The ratio of non-aqueous to aqueous mediums in the mixture may depend upon the type of superabsorbent polymer(s) and fluid mediums that are to be used.

In an alternative embodiment, the superabsorbent polymers may be consolidated into a substantially dehydrated solid device that is delivered to the disc space. Preferably, the solid device is delivered in the form of an elongated shape with as small a cross-section as possible (e.g., small diameter rods no more than about 1 mm in diameter) in order to facilitate delivery to the disc space through a small defect, puncture, or hole in the annulus fibrosis. Also, the superabsorbent solid devices preferably dissolve in vivo to release their constituent superabsorbent polymers into the disc space in order to rehydrate the nucleus.

The solid device may comprise a plurality of unconsolidated particles. In a further embodiment, the solid device may comprise a binder. Preferably, the binder is a bioresorbable polymer that degrades in vivo and releases the superabsorbent polymer. The binder may be mixed with the superabsorbent polymers and then heated and/or pressed to form the shaped solid device. Exemplary binders that may be used in accordance with the embodiments described herein include:

(i) non-resorbable polymers such as poly(urethanes), poly (siloxanes}, poly(methyl methacrylate), poly(ethylene), poly(vinyl alcohol, poly(vinyl pyrrolidon), poly(2-hydroxy ethyl methacrylate), poly(acrylic acid), poly(ethylene-co-vinyl acetate, poly(ethylene glycol), poly(methacrylic acid), and polyacrylamide;

(ii) bioresorbable polymers such as polylactides (PLA), polyglycolides (PGA), poly(lactide-co-glycolides) (PLGA), polyanhydrides, and polyorthoesters;

(iii) natural polymers such as polysaccharides, collagens, silk, elastin, keratin, albumin, and fibrin; and (iv) mixtures and combinations thereof.

In another alternative for making a shaped solid device, the superabsorbent polymers may be mixed with a solvent. The resulting solution may be cast into the shaped solid device and the solvent removed by evaporation, optionally accompanied by heating.

Implanting the solid superabsorbent polymer device may comprise inserting a needle/trocar assembly into the intervertebral disc space, preferably such that the inserted end of the trocar is inside the nucleus pulposus of an intervertebral disc. One or more solid bodies may be placed in the needle/trocar assembly and advanced or pushed through the assembly into the disc space. For example, a stylet or blunt needle may be used to push the solid bodies through the needle/trocar assembly and into the disc space. The needle/trocar then may be removed and the solid device left behind in the disc space. Implanting alternatively may comprise forming an aperture into the intervertebral space of the mammal, and pushing a solid body implant(s) through the aperture and into the intervertebral disc space. Fluoroscopy techniques may be used to guide implantation of the solid device, if desired.

Figure 2:
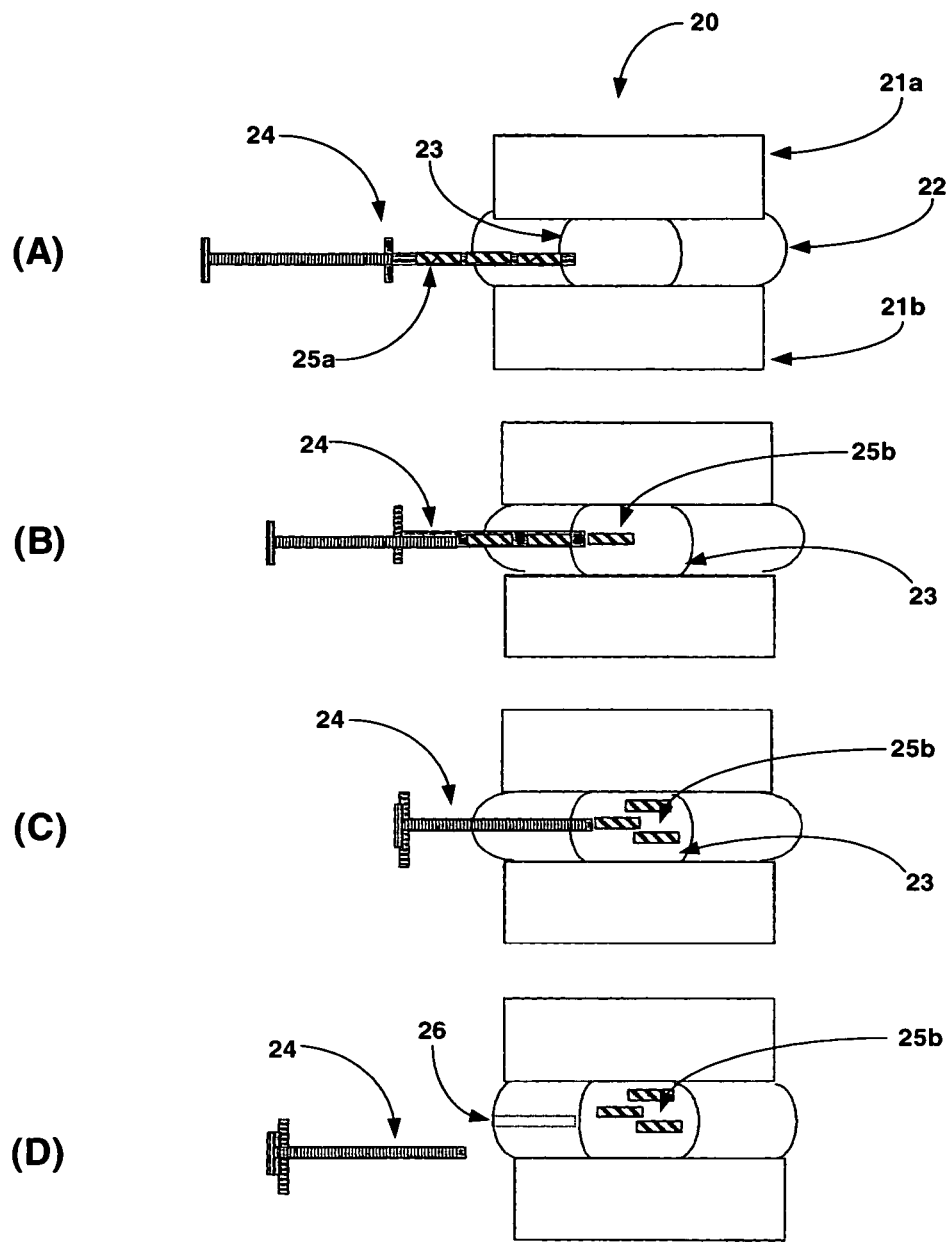
FIG. 2, embodiments A, B, C, and D, illustrates an exemplary "dry" delivery method for introducing superabsorbent polymers to the intervertebral disc space.

Delivery of the superabsorbent polymer to the disc space in the form of a solid device is illustrated by way of example in FIG. 2, embodiments A, B, C, and D. In embodiment A, a delivery device 24 (e.g., a syringe assembly) containing superabsorbent polymer pieces 25a in the form of solid shaped devices, in this case small-diameter rods, is illustrated. The delivery device 24 pierces the annulus fibrosis 22 of the intervertebral disc space 20, which also comprises upper 21a and lower 21b vertebral end plates. Preferably, as shown in embodiment A of FIG. 2, the distal end of the delivery device pierces the nucleus pulposus 23 of the intervertebral disc in order to directly deliver the superabsorbent polymer pieces into the nucleus.

As shown in embodiment B, the delivery device 24 may be depressed or otherwise activated in order to expel the superabsorbent polymer pieces 25b into the nucleus pulposus 23. As shown in embodiment C, the delivery device 24 may expel multiple superabsorbent polymer pieces 25b into the nucleus pulpous 23. However, it should be appreciated that, if desired, only a single superabsorbent polymer piece may be delivered to the disc space. Preferably, sufficient superabsorbent polymer is delivered to the disc space to substantially rehydrate the disc and increase the disc space height, volume, and/or intra-discal pressure.

Embodiment D shows that the delivery device 24 may be removed from the disc space upon delivery of the desired superabsorbent polymer pieces 25b. A hole or defect 26 may be left in the annulus fibrosis upon removal of the delivery device 24. As discussed herein, the defect in the annulus, if desired, may be closed using a subsequent treatment. This may be desirable in order to ensure that the water that is attracted to the disc space by the highly hydrophilic superabsorbent polymer will be retained by the annulus and not allowed to readily exit the disc space.

An X-ray marker optionally may be included in the solid device. The X-ray marker may be used to identify the solid device using fluoroscopy techniques in order to guide delivery of the device into the intervertebral disc. For example, a surgeon may use an appropriate fluoroscopy technique to guide delivery of the solid device directly into the nucleus pulposus of the intervertebral disc. The X-ray marker may comprise any appropriate material detectable by X-ray such as barium sulfate, platinum, tungsten, tantalum, and other bio-compatible materials.

Whether using the "wet" or "dry" delivery methods, it is anticipated that the delivery device may form a puncture, hole, prick, etc., preferably relatively small in size (e.g. ~1 mm in diameter), in the annulus fibrosis in order to deliver the superabsorbent polymer material into the disc space. If desired, the puncture, hole, prick, etc. in the annulus fibrosis may be closed using additional treatment methods. For example, the application of energy via light, heat, or ultrasound may be used to cause the collagen fibers of the annulus to shrink and seal the hole. Alternatively, an occlusion device such as a plug or patch may be used to seal the hole. The occlusion device may be an in vivo formed device or an externally fabricated device that is subsequently surgically placed, preferably using minimally invasive surgical techniques, at the annulus fibrosis. A suitable tissue adhesive or sealant also may be used alone, or together with a plug or patch, to seal the defect in the nucleus. One skilled in the art will appreciate still other techniques by which the hole in the annulus may be treated in order to help ensure proper and speedy healing thereof.

In alternative embodiments, the delivery device may reach the intervertebral disc space via an intrapedicle route. This may be desirable to completely avoid any potential damage to the annulus fibrosis. If needed, a small hole or tap may be drilled in an adjacent vertebral body to facilitate delivery of the superabsorbent polymers by the delivery device. Preferably, however, a bone-piercing delivery device (e.g., certain syringes and needle assemblies are capable of piercing bone) may be used to deliver the superabsorbent polymers via an intrapedicle route. Similar devices and techniques are used in vertebroplasty procedures, and one of skill in the art will appreciate how the vertebroplasty procedures may be adopted to the delivery of a superabsorbent polymer to the disc space, in accordance with the embodiments herein.

When delivering the superabsorbent materials either through an intrapedicle route or through the annulus, preferably an opening of no more than about 5 mm is created in the endplate or annulus. More preferably, an opening of no more than about 3 mm is created in the endplate or annulus. Most preferably, an opening of no more than about 1 mm is created in the endplate or annulus. As has been discussed with particular reference to the annulus, the creation of passages or openings leading to the intervertebral disc desirably is minimized in order to ensure that the superabsorbent polymers that are delivered to the disc space, the water that is attracted to and retained in the disc space by the superabsorbent polymers, and the nucleus pulposus is not able to easily exit the disc space. Therefore, the openings preferably are minimal in number (e.g., preferably only one) and preferably are minimal in size (e.g., preferably only 1 mm or less).

Additionally, whether using "wet" or "dry" delivery methods, it may be desirable to introduce an aqueous solution to the disc space and/or nucleus pulposus following delivery of the superabsorbent polymer material to the disc. Normally, it would be expected that water would be attracted by the highly hydrophilic superabsorbent polymers to the intervertebral disc space via natural routes to the disc space such as seeping through the annulus and micropores in the vertebral endplates and adjacent vertebral bodies. However, it may be desirable to accelerate the rehydration process by directly introducing an aqueous solution to the disc space. For example, a separate delivery device such as a syringe may be used to puncture the annulus and deliver water or a buffered saline solution directly to the disc space.

In further embodiments, various additives may be delivered to the disc space prior to, concurrently with, or subsequent to delivery of the superabsorbent polymers. Additives contemplated for delivery to the disc space include, but are not limited to:

(i) proteoglycans to replace or augment the proteoglycans of the nucleus pulposus;
(ii) growth factors such as transforming growth faction (TGF)-beta, bone morphogenic proteins (BMPs), fibroblast growth factors such as acidic and basic fibroblast growth factor (FGF-1 and -2), platelet-derived growth factors (PDGF) such as PDGF-AB, PDGF-BB, and PDGF-AA, insulin-like growth factors (IGF) such as IGF-I and -II, anti-TNF alpha, lymphokines, FGF-1, FGF-2, FGF4, PDGFs, EGFs, IGFs, OP-1, osteoid-inducing factor (OIF), angiogenin(s), endothelins, hepatocyte growth factor, keratinocyte growth factor, osteogenin (bone morphogenetic protein-3), HBGF- and -2, growth differentiation factors (GDF's), members of the interleukin (IL) family such as IL-1 to IL-6, members of the colony-stimulating factor (CSF) family such as CSF-1, G-CSF, and GM-CSF, and members of the hedgehog family of proteins, including indian, sonic and desert hedgehog;
(iii) cells such as disc cells, annulus cells, nucleus cells, chondrocytes, fibroblasts, nochordal cells, fibroblasts, chondrocytes, and mesenchymal stem cells;
(iv) radiocontrast media such as iodine-containing radiographic contrast agents (e.g., OMNIPAQUE® and HYPAQUE®, both available from Amersham Health, Amersham, United Kingdom);
(v) organic polymers such as polyurethane, polyester, silicone, polyolefin, polyethylene, polyetheretherketone (PEEK), silicone-polyurethane copolymers, polyolefin, polyester, polyethylene oxide, polyethylene glycol, poly (dioxanone), poly(β-caprolactone), poly(hydroxylbutyrate), poly(hydroxylvalerate), tyrosine-based polycarbonate, and polypropylene fumarate;

(vi) carbohydrates, starches, and polysaccharides such as carboxymethyl cellulose, chitin, chitosan, agar, chondroitin sulfate, dermatan sulfate, keratan sulfate, heparan, heparan sulfate, dextran, dextran sulfate, alginate, and hyaluronic acid (vii) crosslinking agents such as:

polyfunctional ethylenically unsaturated cross-linking agents such as N,N'-methylenebisacrylamide, polyethylene glycol di(meth)acrylate, trimethylolpropane tri (meth)acrylate, and divinyl benzene;

polyfunctional cross-linking agents such as epichlorohydrin and related halo epoxy compounds, diglycidyl ether compounds, diisocyanates, polyaldehydes, and polyfunctional amines and imines;

triallylamine, diaziridine compounds, acrylic acid, diiodopropane, dichloropropane, ethylene glycol diglycidyl ether, alkylenebisacylamides, di- and poly-halogenated compounds, and di- or poly-epoxy compounds;

(viii) peptides and proteins such as collagen, gelatin, silk, elastin, keratin, albumin, glycoproteins, lipoproteins, and fibrin; and (ix) other drugs, analgesic compounds, anesthetics, antibacterial compounds, antibiotics such as tetracycline and ciprofloxacin, antibodies, antifungal compounds such as diflucan, ketaconizole and nystatin, anti-inflammatories such as $\alpha$-1-anti-trypsin and $\alpha$-1-antichymotrypsin, antiparasitic compounds such as pentamidine, antiproliferative/cytotoxic drugs such as 5-fluorouracil (5-FU) and taxol, antiviral compounds such as gangcyclovir, zidovudine, amantidine, vidarabine, ribaravin, trifluridine, acyclovir, and dideoxyuridine, anticancer compounds, cytokines such as $\alpha$- or $\beta$- or $\gamma$-Interferon, genetic agents, enzyme inhibitors, hormones, steroids, glucocorticosteroids, immunomodulators, immunoglobulins, minerals, neuroleptics, oligonucleotides, peptides, tumoricidal compounds, tumorstatic compounds, toxins, vitamins and other nutritional supplements, as well as mixtures and combinations of the above-mentioned additives.

As mentioned, cross-linking agents may be included as an additive during delivery of the superabsorbent polymers to the intervertebral disc space. According to the present methods, the superabsorbent polymers may be at least partially crosslinked prior to delivery to the disc space. In other words, the present methods contemplate that the superabsorbent polymers may be crosslinked to form small particulate polymer beads, fibers, flakes, granules, microspheres, nano-particles, particles, pellets, platelets, powder, randomly shaped particles, rods, chunks, or pieces prior to delivery to the disc space. Inclusion of a crosslinking agent with the particulate superabsorbent polymer when it is delivered to the disc space may result in crosslinking between and/or among the SAP particulate matter and other additives. This crosslinking may result in the formation of an aggregate, cross-linked material in the disc space, the aggregate comprising the superabsorbent polymer(s) and optional additive(s) cross-linked by the crosslinking agent(s). This crosslinking may include physical, chemical, ionic, hydrogen-bonding, and/or other forms of crosslinking.

The methods described herein offer several advantages over nucleus replacement, disc replacement, intervertebral fusion, and vertebral fixation procedures. Unlike vertebral fusion and vertebral fixation procedures, rehydration of the nucleus and intervertebral disc space allows the disc to be retained and function in its intended fashion—as an articular joint that both absorbs loads placed on it by the spinal column and permits flexation and rotation of the spinal column. Additionally, vertebral fixation is known to result in stress shielding and stress localization, which may be avoided using the present methods.

The present methods also allow the disc nucleus and annulus to be retained, unlike nucleus replacement and disc replacement procedures. In the present methods, preferably no cutting of the annulus fibrosis or removal of the nucleus occurs. Therefore, there is a decreased likelihood that a large defect would be created in the annulus fibrosis or endplates, which are known to heal only slowly and are not generally capable of being healed after massive trauma. Preferably, the only compromise of the annulus fibrosis that occurs in utilization of the present methods is a small needle prick or hole to insert a cannula or other such device into the disc space in order to deliver the superabsorbent polymer. Furthermore, implantation of nucleus replacement devices typically require comparatively large (e.g., 5 mm-12 mm) holes in the annulus for passage of the device. The present methods allow superabsorbent polymers to be delivered to the disc space through comparatively small (e.g., 1 mm-3 mm) holes in the annulus. Again, this may decrease the likelihood of inflicting permanent injury to the annulus when treating a degenerated or dehydrated intervertebral disc.

A further benefit of the present methods is that removal of the annulus and/or nucleus may result in additional loss of joint strength because of the cutting and removal required. This additional loss of joint strength may result in a substantial weakening of the disc space that cannot be compensated for in terms of mechanical support and functionality. Comparatively, the present methods enable the retention of the nucleus and annulus, and therefore preferably will not result in any further destabilization of the disc space, even if the superabsorbent polymers do not provide the level of rehydration and bulking effects that are hoped for.

Additionally, unlike nucleus replacement and disc replacement devices, the superabsorbent polymers of the present methods preferably do not bear a significant amount of the load placed on the intervertebral disc by the spinal column. Instead, as described herein, the load preferably is born by the rehydrated nucleus and the annulus fibrosis, as would occur in a healthy, normal intervertebral disc. Nucleus and disc replacement devices, in comparison, bear a substantial, if not all, of the load placed on the intervertebral disc and must therefore themselves be of sufficient strength and rigidity to function as intended.

Furthermore, the present methods may be utilized in embodiments wherein the nucleus pulposus and annulus fibrosis are retained. This is advantageous as a simplified procedure compared to the implantation of nucleus and disc replacement devices that may require removal of the nucleus and annulus. For example, the present methods may be accomplished using minimally invasive surgical techniques. Additionally, the present methods may be accomplished using a percutaneous approach to the disc space. These advantages may make the present methods especially desirable for conservative care patients with back or neck pain that are not receptive to surgical intervention. Alternatively, however, some or all of the nucleus and annulus of the intervertebral disc that is to be treated with the present methods may be removed prior to, during, or subsequent to performing the present methods on the disc space. Removal of a portion or all of the nucleus or annulus may be especially desirable where at least a portion of the nucleus or annulus is damaged.

Also, superabsorbent polymers preferably may be delivered to the disc space in accordance with the present methods with or without in-situ crosslinking of the superabsorbent polymers. The present methods additionally contemplate that the superabsorbent polymers may be at least partially crosslinked prior to delivery to the disc space. In other words, the present methods contemplate that the superabsorbent polymers may be crosslinked to form small particulate polymer beads, fibers, flakes, granules, microspheres, nano-particles, particles, pellets, platelets, powder, randomly shaped particles, rods, chunks, or pieces prior to delivery to the disc space. These particulate superabsorbent polymers then may be delivered to the disc space according to the "wet" and "dry" delivery methods described herein. This is unlike the injection of liquid hydrogel-precursor solutions into the intervertebral disc space, because the liquid hydrogel-precursor solutions typically are not crosslinked prior to delivery to the disc space, and undergo significant in-situ crosslinking subsequent to delivery.

Still another benefit of the present methods is the possible restoration of intra-discal pressure. It is believed that, through the osmotic pressure, or hydrophilic action, of the superabsorbent polymer, water may be attracted to and retained in the intervertebral disc space. This may lead to an increase in intra-discal pressure, and preferably to a restoration of intra-discal pressure to its normal state. Intra-discal pressure is thought to be important not only to the basic functioning of the intervertebral disc, but to its general health also. Notably, a reduced intra-discal pressure may lead to destabilization and deterioration of the annulus fibrosis. Therefore, the present methods are thought to reduce the rate of progressive annulus deterioration in an under-inflated intervertebral disc.

The present methods may be used multiple times for treating patients with intervertebral discs that are in need of rehydration. As described herein, the methods provided by the present embodiments may be particularly appropriate to treat mild to moderate degeneration of the intervertebral disc. Following initial treatment with a superabsorbent polymer, subsequent treatment may be periodically scheduled or treatment may be repeated when the disc has again degenerated to the point of requiring additional augmentation or treatment.

Another embodiment provides for the use of an inflatable member to augment and rehydrate a nucleus pulposus of an intervertebral disc. In this embodiment, an inflatable member is inserted into a dilated opening in an intact intervertebral disc annulus and into a nucleus pulposus of the disc. The inflatable member is inserted into the nucleus pulposus in a deflated state, and is connected to an inflation device to controllably inflate the inflatable member within the nucleus pulposus. A superabsorbent polymer material is delivered to the inflatable member by means of the inflation device. Sufficient superabsorbent polymer may be delivered to the inflatable member to cause full, or only partial, or no inflation of the member. Preferably, the superabsorbent polymer is delivered to the inflatable member in a relatively dry state, and then absorbs water after delivery to cause further expansion of the inflatable member. The nucleus pulposus of the intervertebral disc may be either removed or retained, in part or in whole, in this embodiment.

Alternatively, the superabsorbent polymer may be delivered to the inflatable member during or before implantation of the inflatable member in the disc space. In this embodiment, the superabsorbent polymer preferably is delivered to the inflatable member in a dry or partially hydrated state so that the volume of the inflatable member with the superabsorbent polymer inside of it is minimized during implantation.

The inflatable member filled with superabsorbent polymer material desirably causes the nucleus pulposus of the intervertebral disc to expand. In one embodiment, the inflatable member impacts the vertebral end plates of the disc space directly, thereby dilating the end plates and expanding the disc space. In another embodiment, the inflatable member does not impact the vertebral end plates of the disc space directly, and therefore causes expansion of the disc space only indirectly via expansion of the nucleus pulposus into which the inflatable member is implanted. In either case, the inflatable member filled with a superabsorbent polymer and left in a disc space as a permanent implant may cause expansion of the disc space to at least partially restore lost disc height, disc volume, and/or intra-discal pressure.

Preferably, the inflatable member is porous or permeable (e.g., woven fabric, mesh structure, perforated membrane, etc.) in order to allow fluids, such as bodily fluids and aqueous solutions delivered to the intervertebral disc space, to enter the inflatable member. In this way, water may reach the superabsorbent polymer within the inflatable member, causing further expansion of the inflatable member. In another embodiment, aqueous solutions may be delivered directly to the inflatable member by means of another needle or catheter, in order to cause further expansion of the superabsorbent polymer within the inflatable member.

In order to inject the superabsorbent polymer into the inflatable member, it may be necessary to fluidize the polymer material. For example, the superabsorbent polymer may be heated in order to reduce its viscosity such that it becomes sufficiently fluid for injection into the inflatable member. In another embodiment, the superabsorbent polymer may be mixed with a solvent in order to fluidize the polymer. For example, the solvents previously mentioned including water, saline, alcohol, glycerin, ethylene glycol, dimethyl sulfoxide (DMSO), mineral oil, silicone oil, vegetable oil (e.g., canola, corn, and peanut oil), olive oil, and so forth may be used to fluidize the superabsorbent polymer for injection into the inflatable member. Preferably, a non-aqueous solvent is used to fluidize the superabsorbent polymer in order to avoid significant expansion of the polymer before injection into the inflatable member.

The inflatable member may take the form of a balloon of various shapes such as conical, spherical, square, long conical, long spherical, long square, tapered, stepped, dog bone, offset, and combinations thereof. Balloons can be made of various polymeric materials such as polyethylene terephthalates, polyolefins, polyurethanes, nylon, polyvinyl chloride, silicone, polyetheretherketone, polylactide, polyglycolide, poly(lactide-co-glycolide), poly(dioxanone), poly($\epsilon$-caprolactone), poly(hydroxylbutyrate), poly(hydroxylvalerate), tyrosine-based polycarbonate, polypropylene fumarate, and combinations thereof.

The inflatable member may be delivered to the disc space and inflated with the superabsorbent polymer in a number of different ways. For example, one embodiment provides an apparatus including a high-pressure balloon catheter (i.e., the inflatable member) with a small shaft diameter (3 mm or smaller, preferably 2 mm or smaller, and most preferably 1 mm or smaller). The catheter has a pointed tip for puncturing an intact disc annulus and inserting the balloon section into the nuclear pulposus region. The catheter either has a rigid shaft or is supported by a rigid guide-needle during penetration into the disc. For a rigid shaft, the catheter can be made of metal tubing. For a flexible shaft, the catheter can be made of polymeric tubing and is supported with a rigid guide-needle or guide-wire. If a guide-needle is used, the catheter can be double lumen. The balloon has an appropriate final volume of from about 0.1 mL to about 8.0 mL, preferably up to 5.0 mL and dimensions (length from about 5 mm to about 40 mm, preferably from about 10 mm to about 30 mm; and diameter from about 3 mm to about 20 mm, preferably from about 5 mm to about 15 mm) to fit in the nuclear pulposus region of the intervertebral disc.

FIG. 3, embodiments A and B, depicts an exemplary method for treatment of an intervertebral disc space using an inflatable member and a superabsorbent polymer. The disc space 30 comprises endplates 31a and 31b, annulus fibrosis 32, and nucleus pulposus 33. A cannula 34 is connected to an inflatable member 35 that is inserted into the disc space, in this case into the nucleus 33. As shown in embodiment A, the inflatable member 35 may be inserted into the disc space in an substantially deflated form. Then, as shown in embodiment B, a superabsorbent polymer 36 may be injected into the inflatable member 35, for example, via the cannula 34. The superabsorbent polymer 36 may cause the inflatable member 35 to expand to an in-dwelling shape.

In another exemplary balloon catheter, a double lumen balloon catheter can be used for delivery and injection of the balloon. The double lumen balloon catheter includes a first channel, a second channel, and a balloon. The superabsorbent polymer is injected into the balloon via the first channel to inflate balloon for expansion of the disc nucleus. Bodily fluids may reach the superabsorbent polymer inside of the inflatable member by permeating the inflatable member. Alternatively or in conjunction with permeation of bodily fluids, aqueous solutions may be delivered to the superabsorbent polymer directly via the first channel of the double lumen balloon catheter or by injection into the inflatable member using a separate needle/cannula. The balloon then may be detached from the catheter and left inside of the nucleus pulposus when the catheter is withdrawn from the disc space.

Another embodiment provides a method for rehydrating or augmenting an intervertebral disc comprising first determining that the treated disc has a competent and intact annulus fibrosis for safe expansion and effective containment of the subsequently injected superabsorbent polymer. After the annulus quality and integrity are verified, for example using discography, the inflatable member is inserted into the center of the disc. Insertion of the inflatable member can be done percutaneously, preferably under fluoroscopic guidance. The inflatable member then is inflated with radio-contrast fluid or saline to pressurize the disc, and thereby, stretch the annulus fibrosis. After a predetermined inflation time, the balloon is deflated and removed from the disc space. The superabsorbent polymer subsequently is injected into the disc using a small-diameter hypodermic needle until a desirable injection volume is achieved. If desired, an aqueous solution also may be delivered to the superabsorbent polymer. The entire procedure preferably is done under fluoroscopic guidance.

Methods of treating an intervertebral disc using inflatable members are disclosed in U.S. Patent Application Publication No. 2004/0186471, the disclosure of which is incorporated herein by reference in its entirety. In a present embodiment, the superabsorbent polymers provided herein may be used to inflate the inflatable member in accordance with the various embodiments and methods disclosed in the '471 application. Further embodiments herein provide that the inflatable members and superabsorbent polymers may be used, for example, as a compliant core in a total disc replacement device, a nucleus replacement device, as a device to augment a facet joint, as a spacer for separation of interspinous processes, as a filler in expandable spinal rods for partial or full spinal stabilization, and other such embodiments.

The foregoing detailed description is provided to describe the embodiments in detail, and is not intended to limit them. Those skilled in the art will appreciate that various modifications may be made to the embodiments without departing significantly from the spirit and scope thereof.

The invention claimed is:

1. A method for treating an intervertebral disc having a nucleus pulposus and an annulus fibrosis, using one or more partially, chemically crosslinked superabsorbent polymers capable of absorbing fluid in an amount that is at least ten times the weight of the superabsorbent polymer in its dry form, comprising:
   mixing the partially, chemically crosslinked superabsorbent polymers with a binder that degrades in vivo to form a solid device; and
   introducing the solid device into the intervertebral disc space having an intact and competent annuls fibrosis without removing nucleus pulposus or annulus fibrosis material, thereby rehydrating the intervertebral disc space.

2. The method of claim 1, wherein the intervertebral disc is rehydrated until equilibrium swelling is attained.

3. The method of claim 1, wherein the intervertebral disc is at least partially collapsed, and treating the intervertebral disc increases the intervertebral disc's height.

4. The method of claim 1, wherein the intervertebral disc is experiencing progressive disc collapse, and treating the intervertebral disc decreases the rate of disc collapse.

5. The method of claim 1, wherein the intervertebral disc is experiencing progressive disc collapse, and treating the intervertebral disc maintains the intervertebral disc's height.

6. The method of claim 1, wherein the superabsorbent polymers are not more than about 30% crosslinked.

7. The method of claim 6, wherein the superabsorbent polymers are not more than about 10% crosslinked.

8. The method of claim 1, wherein the superabsorbent polymers are in one or more forms selected from the group consisting of beads, fibers, flakes, granules, microspheres, nano-particles, particles, pellets, platelets, powder, randomly shaped particles, rods, chunks, and pieces.

9. The method of claim 1, additionally comprising introducing fluids into the intervertebral disc.

10. The method of claim 1, additionally comprising introducing one or more additives into the intervertebral disc.

11. The method of claim 1, wherein introducing the superabsorbent polymers into the intervertebral disc space comprises:
   mixing the superabsorbent polymers with a medium to make the superabsorbent polymers flowable; and
   using a delivery device to inject the flowable superabsorbent polymers into the disc space.

12. The method of claim 1, wherein introducing the superabsorbent polymers into the intervertebral disc space comprises:
   loading the superabsorbent polymers into a delivery device; and
   using a plunger to force the superabsorbent polymers from the delivery device into the disc space.

13. The method of claim 1, wherein introducing the superabsorbent polymers into the intervertebral disc comprises:
   inserting an inflatable member into the disc space; and
   using a delivery device to inject the superabsorbent polymers into the inflatable member.

14. The method of claim 13, wherein the inflatable member is a balloon.

15. The method of claim 1, wherein mixing the partially, chemically crosslinked superabsorbent polymers with the binder comprises heating the partially, chemically crosslinked superabsorbent polymers and the binder.

16. The method of claim 1, wherein mixing the partially, chemically crosslinked superabsorbent polymers with the binder comprises pressing the partially, chemically crosslinked superabsorbent polymers and the binder to form the solid device.

17. The method of claim 1, wherein the binder comprises bioresorbable polymers selected from a group consisting of: polylactides (PLA), polyglycolides (PGA), poly(lactide-co-glycolides) (PLGA), polyanhydrides, and polyorthoesters.

18. The method of claim 1, wherein the partially, chemically crosslinked superabsorbent polymers comprise polyelectrolytes.

19. The method of claim 1, wherein the partially, chemically crosslinked superabsorbent polymers comprise natural polymers selected from a group consisting of cellulose, starch, and regenerated cellulose; and
the natural polymers are modified to be carboxylated, phosphonoalkylated, sulphoxylated or phosphorylated.

20. The method of claim 1, wherein the partially, chemically crosslinked superabsorbent polymers comprise polyacrylates.

21. A method for bulking up an intervertebral disc having a nucleus pulposus and an annulus fibrosis, using one or more partially, chemically crosslinked superabsorbent polymers capable of absorbing fluid in an amount that is at least ten times the weight of the superabsorbent polymer in its dry form, comprising:
mixing the partially, chemically crosslinked superabsorbent polymers with a binder that degrades in vivo to form a solid device; and
introducing the solid device into the intervertebral disc space having an intact and competent annuls fibrosis without removing nucleus pulposus or annulus fibrosis material, thereby accomplishing at least one of an increase in the disc height, an increase in the disc volume, and an increase in the intra-discal pressure.

22. The method of claim 21, wherein the intervertebral disc is rehydrated until equilibrium swelling is attained.

23. The method of claim 21, wherein the intervertebral disc is at least partially collapsed and bulking up the intervertebral disc increases the intervertebral disc's height.

24. The method of claim 21, wherein the intervertebral disc is experiencing progressive disc collapse, and bulking up the intervertebral disc decreases the rate of disc collapse.

25. The method of claim 21, wherein the intervertebral disc is experiencing disc progressive collapse, and bulking up the intervertebral disc maintains the intervertebral disc's height.

26. The method of claim 21 wherein the superabsorbent polymers are not more than about 30% crosslinked.

27. The method of claim 21, further comprising introducing fluids into the intervertebral disc.

28. The method of claim 21, further comprising introducing one or more additives into the intervertebral disc space.

29. The method of claim 21, wherein mixing the partially, chemically crosslinked superabsorbent polymers with the binder comprises heating the partially, chemically crosslinked superabsorbent polymers and the binder.

30. The method of claim 21, wherein mixing the partially, chemically crosslinked superabsorbent polymers with the binder comprises pressing the partially, chemically crosslinked superabsorbent polymers and the binder to form the solid device.

31. The method of claim 21, wherein the binder comprises bioresorbable polymers selected from a group consisting of: polylactides (PLA), polyglycolides (PGA), poly(lactide-co-glycolides) (PLGA), polyanhydrides, and polyorthoesters.

32. The method of claim 21, wherein the partially, chemically crosslinked superabsorbent polymers comprise polyelectrolytes.

33. The method of claim 21, wherein the partially, chemically crosslinked superabsorbent polymers comprise natural polymers selected from a group consisting of cellulose, starch, and regenerated cellulose; and
the natural polymers are modified to be carboxylated, phosphonoalkylated, sulphoxylated or phosphorylated.

34. The method of claim 21, wherein the partially, chemically crosslinked superabsorbent polymers comprise polyacrylates.

35. A method for augmenting an intervertebral disc comprising:
inserting an inflatable member through the annulus fibrosis into the nucleus pulposus;
inflating the inflatable member to stretch the annulus fibrosis;
deflating the inflatable member;
removing the inflatable member;
mixing partially, chemically crosslinked superabsorbent polymers with a binder that degrades in vivo to form a solid device; and
Introducing the solid device into the nucleus pulposus of the intervertebral disc having an intact and competent annuls fibrosis, wherein the superabsorbent polymer is not more than about 30% crosslinked and wherein the superabsorbent polymer increases the water affinity of the intervertebral disc by absorbing fluid in an amount that is at least ten times the weight of the superabsorbent polymer in its dry form to rehydrate the nucleus pulposus.

36. The method of claim 35, wherein mixing the partially, chemically crosslinked superabsorbent polymers with the binder comprises heating the partially, chemically crosslinked superabsorbent polymers and the binder.

37. The method of claim 35, wherein mixing the partially, chemically crosslinked superabsorbent polymers with the binder comprises pressing the partially, chemically crosslinked superabsorbent polymers and the binder to form the solid device.

38. The method of claim 35, wherein the binder comprises bioresorbable polymers selected from a group consisting of: polylactides (PLA), polyglycolides (PGA), poly(lactide-co-glycolides) (PLGA), polyanhydrides, and polyorthoesters.

39. The method of claim 35, wherein the partially, chemically crosslinked superabsorbent polymers comprise polyelectrolytes.

40. The method of claim 35, wherein the partially, chemically crosslinked superabsorbent polymers comprise natural polymers selected from a group consisting of cellulose, starch, and regenerated cellulose; and
the natural polymers are modified to be carboxylated, phosphonoalkylated, sulphoxylated or phosphorylated.

* * * * *

UNITED STATES PATENT AND TRADEMARK OFFICE
CERTIFICATE OF CORRECTION

| | | |
|---|---|---|
| PATENT NO. | : 8,801,790 B2 | Page 1 of 1 |
| APPLICATION NO. | : 11/316974 | |
| DATED | : August 12, 2014 | |
| INVENTOR(S) | : Trieu | |

It is certified that error appears in the above-identified patent and that said Letters Patent is hereby corrected as shown below:

In the Specification

Column 12, Line 47, delete "FGF4," and insert -- FGF-4, --, therefor.

Column 13, Line 1, delete "poly(β-caprolactone)," and insert -- poly(ε-caprolactone), --, therefor.

Signed and Sealed this
Twenty-first Day of October, 2014

Michelle K. Lee
*Deputy Director of the United States Patent and Trademark Office*